United States Patent
Liao et al.

(10) Patent No.: US 8,562,619 B2
(45) Date of Patent: Oct. 22, 2013

(54) INJECTABLE THERMOPLASTIC POLYMERS FOR BIOLOGICAL TISSUE REPAIR

(75) Inventors: Chun-Jen Liao, Taipei (TW); Yang-Hwei Tsuang, Taipei (TW); Huang-Chien Liang, Hsinchu (TW); Chun-Hung Chen, Baoshan Township, Hsinchu County (TW); Fon-Yih Tsuang, Taipei (TW); Yi-Jie Kuo, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 710 days.

(21) Appl. No.: 12/630,078

(22) Filed: Dec. 3, 2009

(65) Prior Publication Data
US 2011/0137318 A1  Jun. 9, 2011

(51) Int. Cl.
*A61B 17/56* (2006.01)
*A61F 2/28* (2006.01)

(52) U.S. Cl.
USPC .................. 606/92; 623/23.58; 623/23.62

(58) Field of Classification Search
USPC ........ 606/92–94, 76–77; 604/113; 623/23.62, 623/23.58
See application file for complete search history.

(56) References Cited

U.S. PATENT DOCUMENTS

| | | | |
|---|---|---|---|
| 5,946,370 A | 8/1999 | Adler et al. | |
| 6,048,346 A | 4/2000 | Reiley et al. | |
| 6,066,154 A | 5/2000 | Reiley et al. | |
| 6,235,043 B1 | 5/2001 | Reiley et al. | |
| 6,241,734 B1 | 6/2001 | Scribner et al. | |
| 6,607,544 B1 | 8/2003 | Boucher et al. | |
| 6,662,148 B1 | 12/2003 | Adler et al. | |
| 7,377,934 B2 | 5/2008 | Lin et al. | |
| 2005/0288795 A1* | 12/2005 | Bagga et al. | 623/23.51 |
| 2007/0027230 A1* | 2/2007 | Beyar et al. | 523/117 |
| 2007/0191963 A1 | 8/2007 | Winterbottom et al. | |
| 2009/0131947 A1* | 5/2009 | Aeschlimann et al. | 606/93 |

FOREIGN PATENT DOCUMENTS

TW   92110213   4/2003

OTHER PUBLICATIONS

Matbase, "Polylactic Acid (PLA)", accessed Jul. 5, 2012 at http://www.matbase.com, pp. 1-2.*
Lewis G., Injectable bone cements for use in vertebroplasty and kyphoplasty: state-of-the-art review. J Biomed Mater Res B Appl Biomater. 2006; 76(2):456-68.
Wilke H.J., et al. Biomechanical evaluation of vertebroplasty and kyphoplasty with polymethyl methacrylate or calcium phosphate cement under cyclic loading. Spine. 2006; 31(25):2934-41.
Stanczyk M., et al. Thermal analysis of bone cement polymerisation at the cement-bone interface Journal of biomechanics, 2004;37(12):1803-10.

(Continued)

*Primary Examiner* — Michael T Schaper
(74) *Attorney, Agent, or Firm* — Cesari & McKenna, LLP (57) ABSTRACT

A method for filling a bone defect in a subject in need thereof is disclosed. The method includes heating a bone cement composition at a first temperature where the bone cement composition is fluidic, and delivering an effective amount of the fluidic bone cement composition at a second temperature to the bone defect thereby filling the bone defect and allowing the fluidic bone cement composition to solidify, the second temperature being sufficiently high for maintaining the bone cement composition fluidic without causing thermal necrosis. Also disclosed are systems for carrying out the method.

5 Claims, 6 Drawing Sheets

(56) References Cited

OTHER PUBLICATIONS

Deramond H., Temperature elevation caused by bone cement polymerization during vertebroplasty. Bone. 1999;25(2):17S-21S.

Yang JM. Polymerization of acrylic bone cement using differential scanning calorimetry. Biomaterials. 1997;18(19):1293-8.

Ping L. Studies on the synthesis and thermal properties of copoly(L-lactic acid/glycolic acid) by direct melt polycondensation. Journal of Applied Polymer Science. 2004;92:2163-2168.

Taiwanese Office Action (Mail Date: May 29, 2013) for Taiwanese patent application No. 099116108 filed on Dec. 3, 2009. By Industrial Technology Research Institute, 10 pages—No translation available.

* cited by examiner

INJECTABLE THERMOPLASTIC POLYMERS FOR BIOLOGICAL TISSUE REPAIR

FIELD OF THE INVENTION

The invention relates to methods for repairing biological tissues, in particular, bone tissues. The invention also relates to devices for practicing the methods of the invention.

BACKGROUND

Osteoporotic and non-osteoporotic vertebral body compression fractures are currently treated with vertebroplasty and kyphoplasty. See, G. Lewis, *J Biomed Mater Res Part B: Appl Biomater* 76(2): 456-468, 2006.

In vertebroplasty, an acrylic cement (e.g., a monomeric cement such as methyl methacrylate cement) is injected through a small hole in the skin (i.e., percutaneously) into a fractured vertebra to stabilize it. Kyphoplasty involves placement of a balloon into a collapsed vertebra before the injection of bone cement to stabilize the fracture.

One of the common risks associated with both vertebroplasty and kyphoplasty is leakage of acrylic cement to the outside of the vertebral body, causing infection, bleeding, numbness, tingling, headache, paralysis, heart damage, lung damage, and even death. Also, polymers formed of certain monomeric acrylic cements used in vertebroplasty and kyphoplasty do not promote growth of new bone tissues due to lack of adequate porosity and biodegradability.

For these and other reasons, there is a need for new approaches to placing into defected bones (e.g., fractured vertebrae) a biocompatible material that not only has little or no toxicity but also has an adequate porosity to allow bone growth and thus accelerates bone healing.

SUMMARY

In one aspect, the invention relates to a method for tissue repairing, in particular, filling a bone defect in a subject in need thereof, e.g., a human subject suffering from vertebral body compression fractures. The method includes heating a bone cement composition at a first temperature where the bone cement composition is fluidic; and delivering an effective amount of the fluidic bone cement composition at a second temperature to the bone defect thereby filling the bone defect and allowing the fluidic bone cement composition to solidify, the second temperature being sufficiently high for maintaining the bone cement composition fluidic without causing thermal necrosis.

As used herein, the term "a" or "an" refers to one or more. For example, the term "a second temperature" refers to both a temperature point and a range of temperatures. The term "effective amount" refers to the amount of the bone cement composition needed in one administration to elicit the desired defect-filling effect without causing thermal necrosis when the composition releases heat during solidification. Depending on the heat released by a bone cement composition per unit weight, the effective amount administered varies. Typically, the effective amount varies between 1 mL and 10 mL (e.g., 1.2-7 mL). In the event that the effective amount is less than the required amount to fill a bone defect, one can administer two or more times the effective amount of the bone cement composition to the defect, thereby filling it and exerting support to the bone. The term "without causing thermal necrosis" refers to causing little or no thermal necrosis to the normal tissues or organs surrounding the bone defect.

Embodiments of the method may include one or more of the following features.

The bone cement composition includes a thermoplastic biocompatible polymer.

The thermoplastic biocompatible polymer can have a glass transition temperature ranging from 20° C. to 120° C. (e.g., 30° C. to 80° C.), or can be an amorphous polyester such as poly(DL-lactic acid), or can be a combination of two or more amorphous polyesters. The term "combination" refers to a blend or copolymer. The thermoplastic biocompatible polymer can be biodegradable. The thermoplastic biocompatible polymer can be poly(lactic-co-glycolic acid) (PLGA), polylactic acid (PLA), poly glycolic acid (PGA), poly(β-hydroxyl butyrate) (PHB), poly alkylene succinates, poly (butylene diglycolate), poly (ε-caprolactone), or a combination thereof. The thermoplastic biocompatible polymer can have a melting point of 70° C. to 200° C. The first temperature can range from the melting point of the thermoplastic biocompatible polymer to 250° C. The second temperature can ranges from 30° C. to 80° C.

The bone cement composition can further include a biocompatible salt containing calcium, such as calcium phosphate (e.g., beta tricalcium phosphate) or calcium sulfate. The weight ratio of the salt to the thermoplastic polymer can be 1:10 to 5:1 (e.g., 1:3 to 2:1).

As used herein, a polymer is biocompatible if the polymer and any degradation products of the polymer are generally non-toxic to the recipient and also possess no significant deleterious or untoward effects on the recipient's body, such as a significant immunological reaction at the injection site. "Biodegradable," as defined herein, means the composition will degrade or erode in vivo to form smaller chemical species. Degradation can result, for example, by enzymatic, chemical, or physical processes.

In another aspect, the invention relates to a system for delivering a bone cement composition to a bone defect in a subject in need thereof. The system includes an inlet for receiving a bone cement composition, the composition including a thermoplastic biocompatible polymer and optionally a biocompatible salt containing calcium; an outlet for dispatching the bone cement composition, a conduit for conveying the bone cement composition from the inlet to the outlet, a piston enclosed in the conduit, a heater configured to be in thermal communication with the conduit, and a driver configured to move the piston along the conduit for forcing the bone cement composition received from the inlet out of the conduit via the outlet.

The details of one or more embodiments are set forth in the accompanying description below. Other aspects, features, and advantages will be apparent from the following drawing, detailed description of embodiments, and also from the appending claims.

DETAILED DESCRIPTION

This invention relates to a method for repairing a bone defect in a subject in need thereof by injecting a molten bone cement composition into the defect, thereby filling it upon solidification of the composition. Preferably, the composition includes a thermoplastic biocompatible polymer, such as PLGA, and optionally a biocompatible salt containing calcium, such as calcium phosphate (e.g., beta tricalcium phosphate) or calcium sulfate.

The bone cement composition can be prepared via conventional method. In one embodiment, the composition is prepared by mixing PLGA and tricalcium phosphate (TCP). More specifically, PLGA is first dissolved in dichloromethane (DCM) to afford a viscous solution (30%, w/v); next, TCP and NaCl are added into the solution; the resulting mixture is stirred to form a homogeneous solution; the solvent is then removed to form a dried mixture, which is then rinsed with deionized water to remove water-soluble salts (e.g., NaCl); the desalted mixture is subsequently dried (e.g., lypholized) to obtain PLGA/TCP powders. The as-formed PLGA/TCP powders can further be sterilized. The method is described in greater detail in U.S. Pat. No. 6,824,716.

As indicated above, bone cement compositions used in the methods of this invention are compositions that become fluidic during their delivery into a bone defect and cause no thermal necrosis during solidification. Suitable compositions are thus selected by evaluating, e.g., their thermodynamic and rheological properties. Conventional methods can be used for the evaluation. For example, differential scanning calorimetry (DSC) can be used to evaluate thermodynamic properties of the thermoplastic polymer in the bone cement composition, such as glass transition temperature (Tg), crystallization temperature (Tc), and melting point (Tm). The heat released/absorbed during a phase transition (e.g., from a liquid phase to a solid phase) can also be determined using DSC. In one embodiment, 3-5 mg of bone cement composition is tested using PerkinElmer Diamond DSC under nitrogen (flow rate 50 ml/min) at a temperature range of 0~250° C. (temperature ramping rate 10° C./min). Indium standard (mp: 156.4° C. and ΔH, fusion: 6.8 cal/g) can be used for calibration. The rheological properties of the bone cement compositions can be reflected by their melt flow indexes (MFI, also known as melt flow rate). The testing method is given in ASTM D1238 and ISO 1133 (similar). MFI is a measure of the ease of flow of the melt of a thermoplastic polymer. It is defined as the mass (in grams) or volume (in liters) of polymer flowing in 10 minutes through a capillary of specific diameter and length by a pressure applied via prescribed alternative gravimetric weights for alternative prescribed temperatures. A higher MFI value indicates a higher fluidity.

Figure 1:
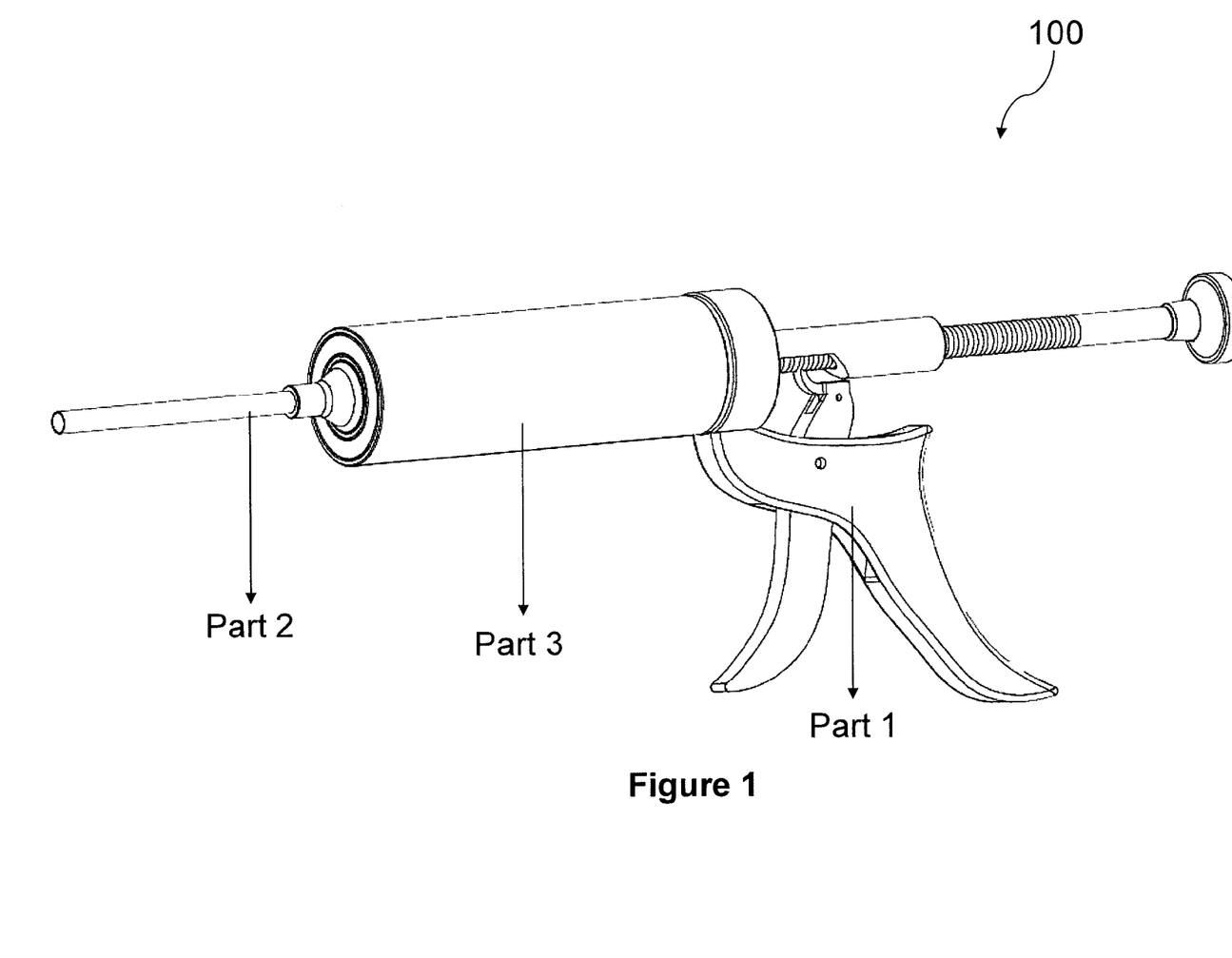
FIG. 1 is a perspective view of an embodiment of the bone cement delivering system of the invention.

The suitable bone cement composition used in this invention can be delivered to a bone defect via a system including an inlet for receiving a bone cement composition, an outlet for dispatching the bone cement composition, a conduit for conveying the bone cement composition from the inlet to the outlet, a piston enclosed in the conduit, a heater configured to be in thermal communication with the conduit, and a driver configured to move the piston along the conduit for forcing the bone cement composition received from the inlet out of the conduit via the outlet. In one embodiment, the method of this invention is carried out in device 100 as shown in FIG. 1.

The device includes three segments, i.e., Part 1, a driving mechanism, Part 2, a conduit for delivering bone cement, and Part 3, a heater.

Figure 2A:
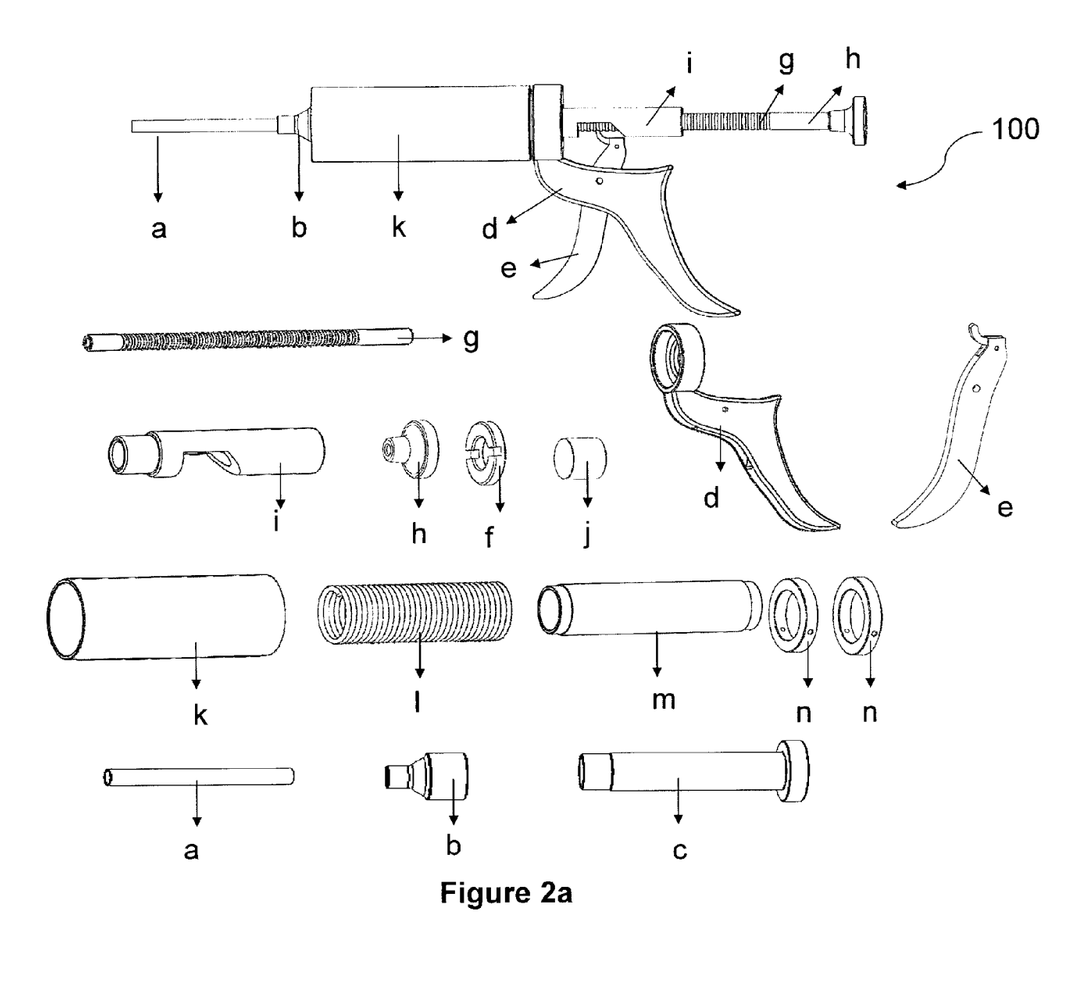
FIG. 2a is a perspective view of the components of the system in FIG. 1.
Figure 3:
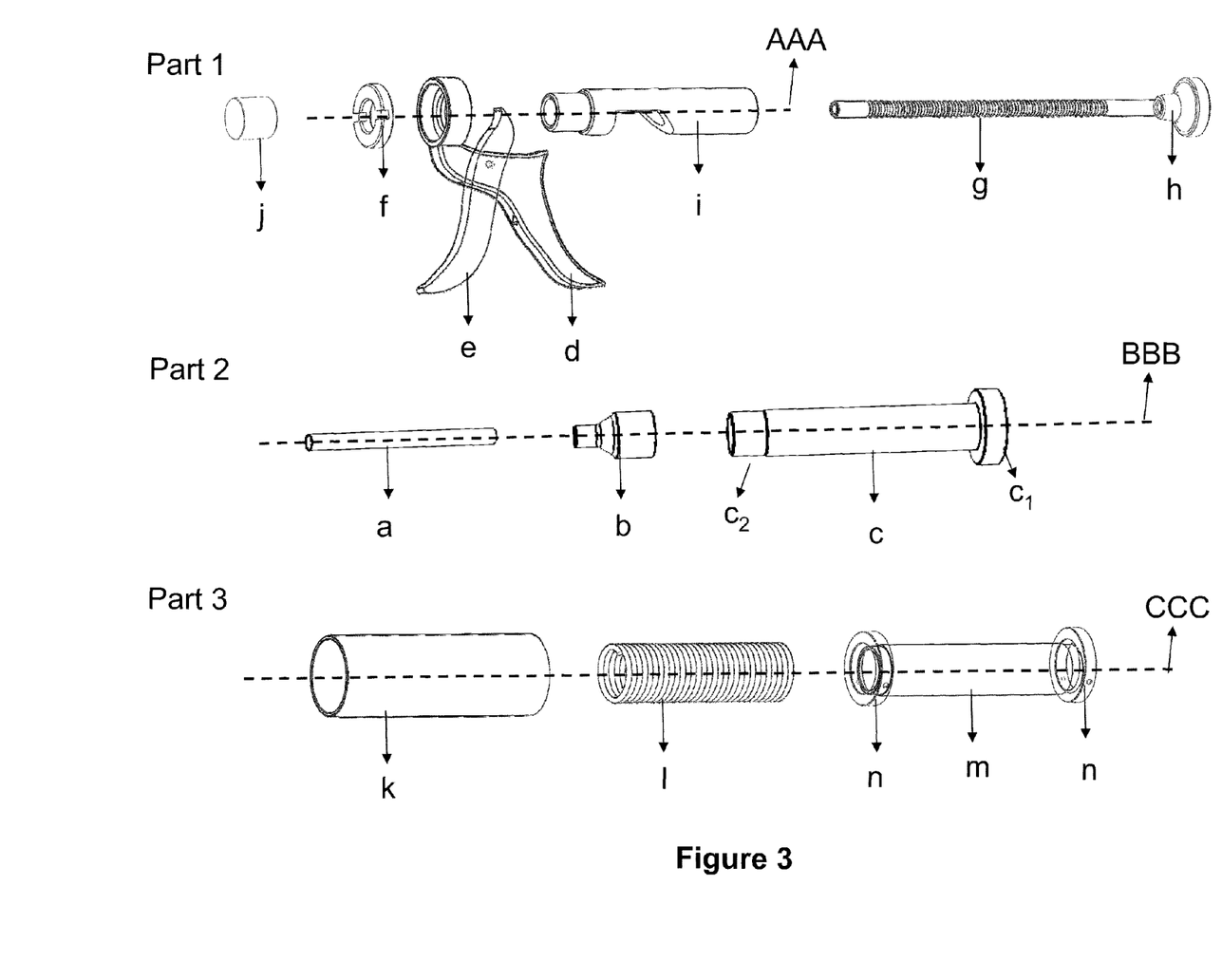
FIG. 3 is a schematic of the assembly of the system in FIG. 1.

Part 1, as illustrated in FIGS. 2a and 3, the driving mechanism, includes piston head (j), gear rod (g), pull end (h), shaft (d), piston driver (e), washer (f), and driver holder (i). The gear rod (g) is housed within the driver holder (i) and engaged with piston driver (e) in the open window of holder (i). The piston driver (e) is mounted on the shaft (d) via a pivot so that when force is applied at the distal end of the driver (e), the proximal end, which is engaged with gear rod (g), will drive the gear rod to move along the axis AAA. The driver holder (i) is locked into the shaft (d) via the washer (f).

The gear rod (g) has a suitable pitch to prevent excessive gap during each push action. The diameter of the gear rod (g) was smaller than that of the piston head (j) to reduce friction. Preferably, as demonstrated in FIG. 2b, the proximal end of the driver (e) includes a mechanism 10, which prevents the gear rod from moving backward when the force 20 on the driver (e) is released. One benefit of including mechanism 10 is the increased convenience of using the device 100 to inject the molten cement into the defect.

Part 2, as also shown in FIGS. 2a and 3, includes main tube (c), nozzle (b), and extension tube (a). The main tube (c) has a first open end ($c_1$) and a second open end ($c_2$) opposed to $c_1$. The first open end is connected to the ring structure of shaft (d). The second end is connected to nozzle (b), which in term is connected to extension tubes (a). The main tube (c) has an inner diameter that corresponds to the outer diameter of the piston head (j) so that the piston head can force out the material contained in the main tube (c) when it moves along the axis AAA inside the main tube. The extension tube (a) is preferably made of heat insulating material or configured to be heat insulating so that the tube can both keep the heated composition contained therein fluidic and also cause no thermal necrosis to the tissues it contacts. For example, the extension tube (a) may have contain a vacuum layer inside its wall or may have an outer insulation layer. In embodiments, tube (a) has a length of is 3-10 cm and an inner diameter of 4-6 mm; nozzle (b) has a length of 2-3 cm, and tube (c) has a length of 9-10 cm and an inner diameter of 1.3-1.5 cm.

Figure 2B:
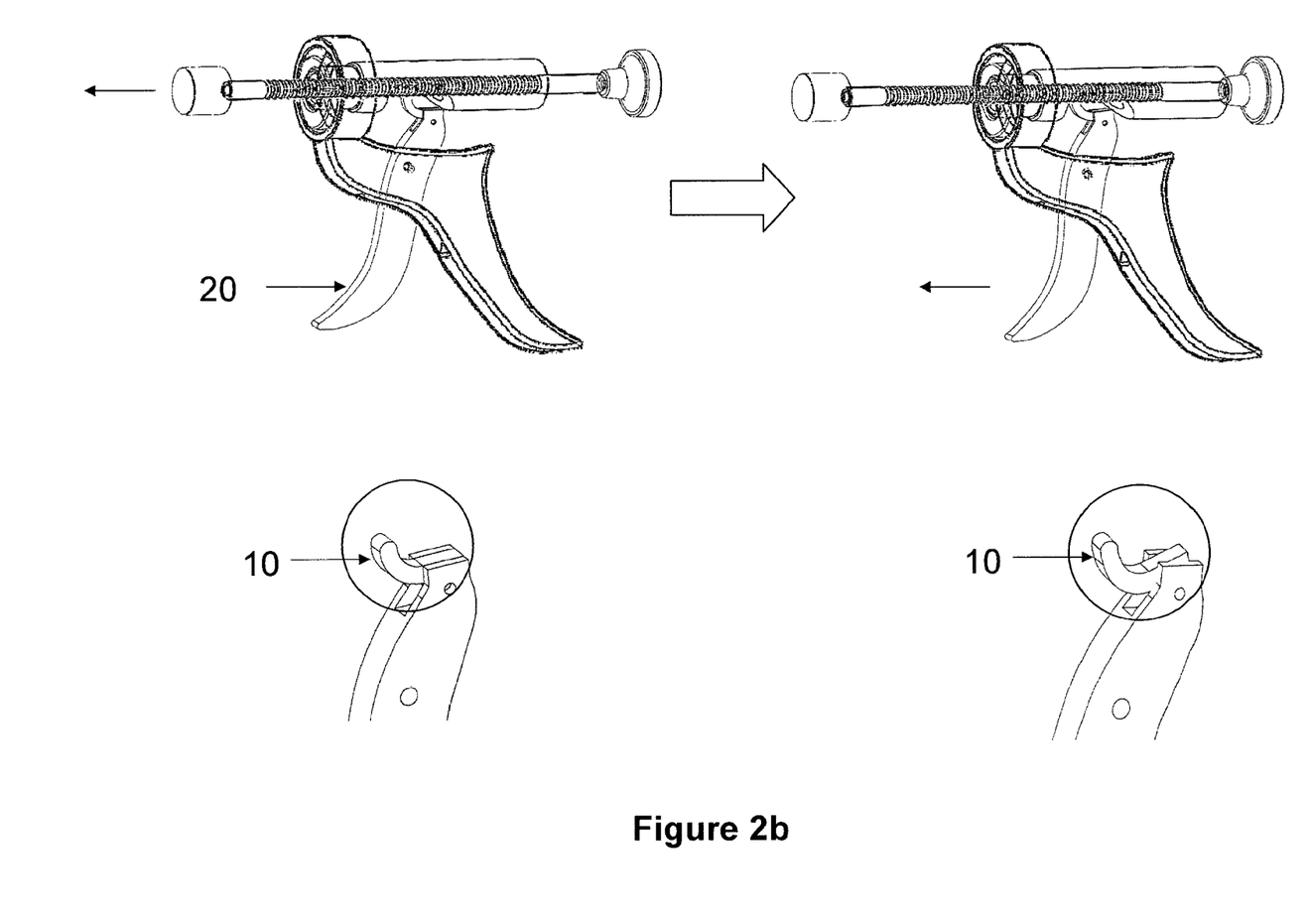
FIG. 2b is a schematic of the piston driver of the system in FIG. 1.

As also shown in FIGS. 2 and 3, Part 3, the heater, includes heat conducting tube (m), insulation tube (k), coil heater (l) with an embedded thermocouple sensor sandwiched between tubes (m) and (k), and two flanges (n). The coil heater (l) covers the whole length of heat conducting tube (m). The embedded thermocouple sensor (not shown) allows programmable control of the heating process. The flanges (n) positioned at both side of the conducting tube (m) are used to sustained the heat generated by coil heater (l) within insulation tube (k). The heat conducting tube (m) houses the main tube (c) of Part II to ensure a uniform temperature gradient.

Figure 4:
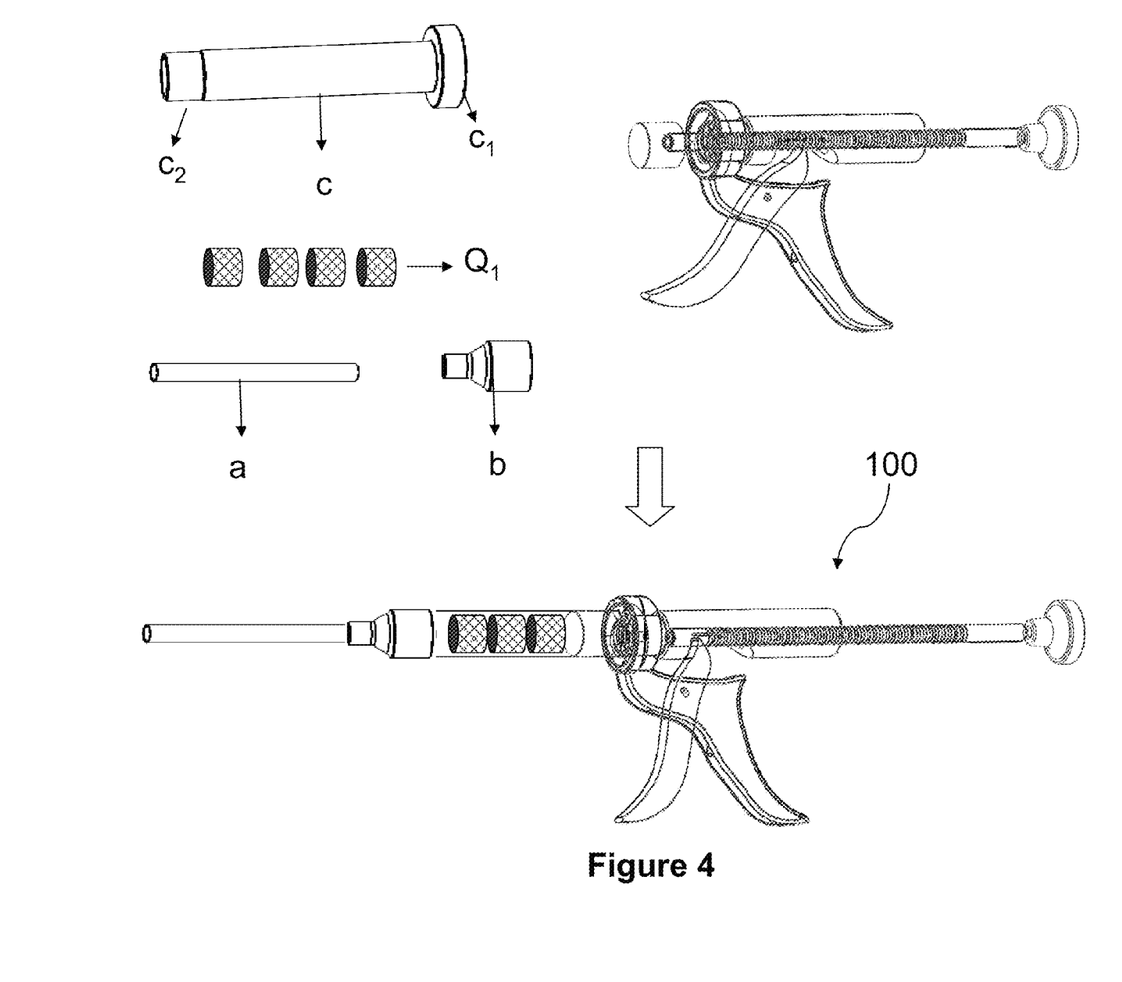
FIG. 4 is a schematic of loading a bone cement composition in the system in FIG. 1.
Figure 5:
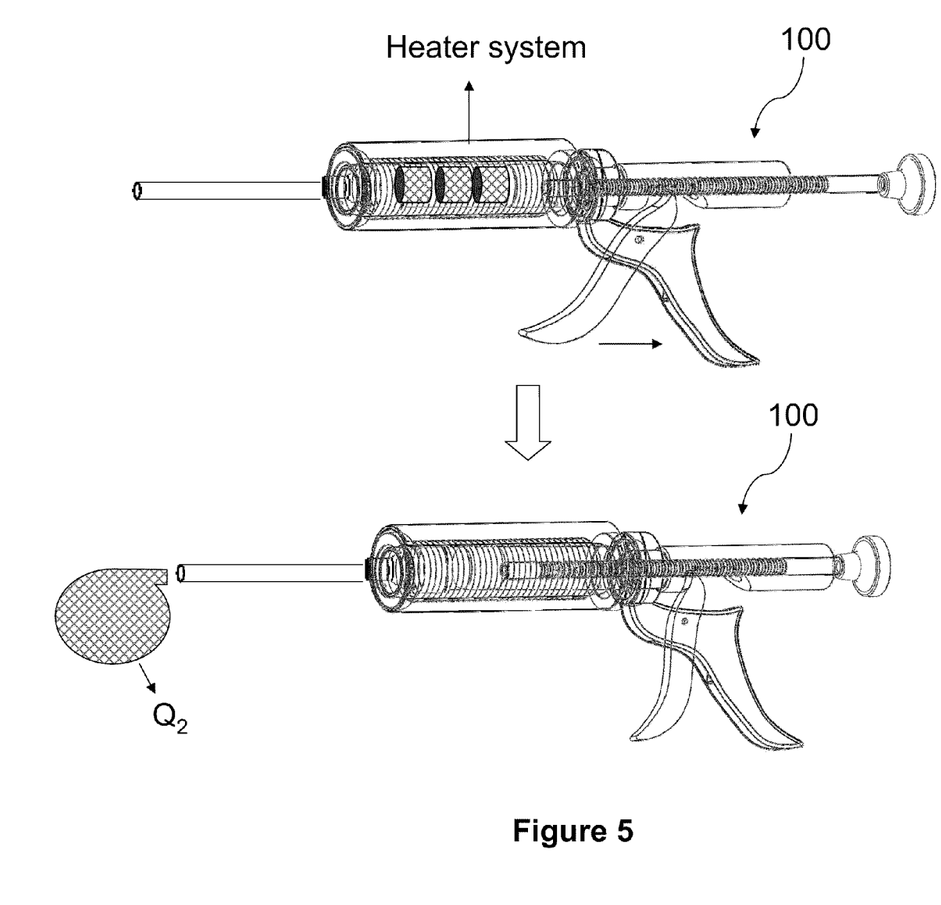
FIG. 5 is a schematic of using the system in FIG. 1 to deliver a bone cement composition.

As shown in FIG. 4, the solid material to be delivered ($Q_1$), e.g., a bone cement composition is loaded in the delivery system 100 by placing $Q_1$ into the main tube (c). When the tube (c) is pre-installed onto the Part 1, $Q_1$ is loaded from the second open end ($c_2$), following which, the nozzle (b) and extension tube (a) are installed. Part 3 is then placed around the main tube (c) to provide thermal energies required for transforming $Q_1$ into its fluidic phase. As shown in FIG. 5, when the material Q1 transforms into its liquid phase $Q_2$, a force applied on Part 1 can drive the materials $Q_2$ out of the device 100 thereby delivering Q2 to a predetermined site. In embodiments, solid material to be delivered ($Q_1$) can be directly used without pre-mixed thoroughly. Advantages of doing so include reducing surgical time and reducing likelihood of contamination.

When using the system of this invention to precisely deliver the molten bone cement composition to a bone defect, a guiding catheter can be used to precisely dispose the extension tube (a) proximate to or in the defect. The inner diameter of the extension tube (a) matches the outer diameter of the guiding catheter.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

The thermodynamic properties of PLGA/TCP powders and Simplex® P acrylic bone cement purchased from Stryker Inc. as control group were tested using Diamond DSC from PerkinElmer. The test conditions were set as follows: nitrogen flow rate 50 ml/min, temperature range 0~250° C., and ramping rate 10° C./min. The results are provided in Table 1 and Table 2 below.

TABLE 1

Phase transition temperatures

| Composition | Tg (° C.) | Tm (° C.) |
|---|---|---|
| PLGA (100%) | 67 | 148 |
| PLGA/TCP (75%/25%) | 64.78 | 147.1 |
| PLGA/TCP (50%/50%) | 61.2 | 146.8 |
| PLGA/TCP (33%/67%) | 60.43 | 145.05 |

TABLE 2

Heat released during solidification

| Composition | $\Delta H_{ideal}$ (Jg$^{-1}$) | $\Delta H_{real}$ (Jg$^{-1}$) | Weight (mg) | Total Heat (mJ) |
|---|---|---|---|---|
| PLGA/TCP(33%/67%) | 42.4 | 29.8 | 7.86 | 234.7 |
| Simplex ® P bone cement | 72.98 | 79.7 | 7.5 | 598.2 |

Unexpectedly, adding TCP into PLGA resulted in a decrease in Tg, and the heat released by PLGA/TCP (33%/67%) was less than half of that released by the acrylic bone cement of the same weight when they transformed from liquid forms to solid forms.

EXAMPLE 2

The melt flow indexes of PLGA/TCP powders were determined following ASTM D1238.

Table 3 below shows the MFI values of the tested compositions.

TABLE 3

Melting flow indexes

| PLGA/β-TCP Ratio | MFI (mL/10 min.) |
|---|---|
| 100%/0% | 1.55 |
| 75%/25% | 0.76 |
| 33%/67% | 0.159 |

Conditions: T = 155° C., P = 13000 psi

As indicated by the results listed in Table 3, an increase in TCP content led to a decrease in fluidity. In other words, the temperature and pressure required for producing a fluidic phase increased with increasing TCP content in the composition.

EXAMPLE 3

A prototype device of FIG. 1 was tested for transforming and delivering a bone cement composition. The results were shown in Table 4 below.

TABLE 4

| Composition | Heating temperature (° C.) | Heating duration (min) | Outflow temperature (° C.) |
|---|---|---|---|
| PLGA | 200 | 10 | 100 |
| PLGA/TCP (75%/25%) | 215 | 10 | 103 |
| PLGA/TCP (50%/50%) | 220 | 15 | 105 |
| PLGA/TCP (33%/67%) | 225 | 10 | 107 |

EXAMPLE 4

The biological properties of bone cement compositions were evaluated following the method set forth in ISO 10993, biological evaluation of medical devices, part 6: test for local effects after implantation.

Two 3-month old New Zealand white rabbits (2.4~2.8 Kg/each) were administered with a mixture of Ketamine (0.4 ml/kg) and Xylazine (Rompun, 0.4 ml/kg) for general anesthesia via a muscle injection. Xylocalne (2%) was also administered for local anesthesia via a subcutaneous injection at the surgical site. After iodine sterilization, an incision was made in the skin above the femoral condyle and a hole of 6 mm in diameter was drilled in the femoral condyle while the skin and surrounding muscle were kept open by Weitlaner retractor. After removing splinters with a saline, a bone cement composition was introduced. The outer surface of the composition was in a close contact with the compact bone. In one of the two rabbit, the left leg was implanted with molten PLGA/PCT (33%/67%) and the right leg with a commercially-available bone cement (Simplex P, Stryker Inc.). In the other rabbit, the compositions for each leg were switched to reduce differences caused by positions. The incision was then closed up with absorbable and Nylon sutures. The sutured wound was then sterilized with iodine and covered with gauzes to prevent infection. After the surgery, Calcein dye and Tetracycline were administered alternately every week.

One month post surgery, the rabbits were sacrificed. The body parts with the bone cement implants were taken out and fixed with 10% neutralized formaldehyde. After removing fat and calcium, the tissue was embedded in paraffin and stained with Hematoxyline and Eosin (H&E). The nucleus and non-nucleus cellular components were stained with different colors. The nucleus appeared purple and all non-nucleus cellular components appeared pink. The results from H&E Stain showed that neither the commercial acrylic bone cement nor the PLGA/TCP composition caused any infection or inflammation. Also, the results indicated that new connective tissues had grown around the bone tissues where the bone cement compositions were injected, both in the PLGA/TCP group and the commercial cement group.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for filling a bone defect in a subject in need thereof, the method comprising:

heating a bone cement composition to a first temperature where the bone cement composition is fluidic, wherein the bone cement composition contains (i) a thermoplastic biocompatible polymer, which is poly(lactic-co-glycolic acid) (PLGA) and (ii) a biocompatible salt containing calcium, the first temperature ranging from 200° C. to 250° C. and the weight ratio of the salt to the polymer being 1:3 to 2:1; and delivering an effective amount of the fluidic bone cement composition at a second temperature to the bone defect thereby filling the bone defect and allowing the fluidic bone cement composition to solidify, the second temperature being sufficiently high for maintaining the bone cement composition fluidic without causing thermal necrosis.

2. The method of claim 1, wherein the biocompatible salt is calcium phosphate or calcium sulfate.

3. The method of claim 2, wherein the calcium phosphate is beta tricalcium phosphate.

4. The method of claim 3, wherein the weight ratio of the salt to the polymer is 2:1.

5. The method of claim 1, wherein the second temperature ranges from 30° C. to 80° C.

* * * * *